(12) United States Patent
Matsui et al.

(10) Patent No.: US 7,535,562 B2
(45) Date of Patent: May 19, 2009

(54) APPARATUS AND METHOD FOR DEFECT INSPECTION

(75) Inventors: Shigeru Matsui, Hitachinaka (JP); Masaaki Ito, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 424 days.

(21) Appl. No.: 11/437,643

(22) Filed: May 22, 2006

(65) Prior Publication Data

US 2006/0262297 A1    Nov. 23, 2006

(30) Foreign Application Priority Data

May 23, 2005    (JP)    ............................. 2005-148885

(51) Int. Cl.
*G01N 21/00*    (2006.01)
(52) U.S. Cl. ................................. 356/237.5; 356/237.2
(58) Field of Classification Search ........................ None
See application file for complete search history.

(56) References Cited

U.S. PATENT DOCUMENTS 5,450,201 A * 9/1995 Katzir et al. ................. 356/369
5,719,405 A * 2/1998 Hayano ................. 250/559.41
7,301,622 B2 * 11/2007 Geh et al. ................. 356/239.2
2004/0100629 A1 * 5/2004 Stokowski et al. ........ 356/237.2
2004/0165182 A1 * 8/2004 Brunner et al. .......... 356/237.5
2005/0195398 A1 * 9/2005 Adel et al. ................. 356/401

FOREIGN PATENT DOCUMENTS

JP    2000-155099 A    6/2000

* cited by examiner

*Primary Examiner*—Michael P Stafira
(74) *Attorney, Agent, or Firm*—McDermott Will & Emery LLP

(57) ABSTRACT

In the conventional methods for enhancing defect detection sensitivity by improving the resolving power, if a microscopic pattern, which is a high spatial-frequency structure as is the case with a microscopic defect, has become the brightest portion, the gray-scale contrast of the microscopic defect will be enhanced. At the same time, however, the gray-scale contrast of the microscopic pattern will also be enhanced simultaneously. Consequently, there has existed a problem that it is impossible to enhance the microscopic-defect detection sensitivity further than that. In the present invention, an aperture stop which is divided into a plurality of small apertures is located on an illumination pupil plane. Then, light-shield/light-transmission for each small aperture is controlled independently of each other. This control allows an inspection-target object to be illuminated at only an incident angle at which the gray-scale contrast of the microscopic defect will be emphasized more sharply.

14 Claims, 8 Drawing Sheets

80

LIGHT-TRANSMITTING PORTION

LIGHT-SHIELDING PORTION

APPARATUS AND METHOD FOR DEFECT INSPECTION

BACKGROUND OF THE INVENTION

1. Field of the Invention

The present invention relates to a defect inspection apparatus and method for inspecting defects existing on an inspection-target object. More particularly, it relates to a defect inspection apparatus and method used for observing and inspecting defects and foreign substances on microscopic patterns in fabrication lines such as semiconductor fabrication steps and flat-panel display manufacturing steps.

2. Description of the Related Art

In the fabrication lines such as semiconductor fabrication steps and flat-panel display manufacturing steps, the observation and inspection of the defects and foreign substances on microscopic patterns are performed using optical microscopes. From the viewpoint of illumination schemes, the microscope optics used for the defect inspection like this are classified into two types, i.e., bright-field illumination scheme and dark-field illumination scheme. Here, the bright-field illumination scheme is a scheme which takes in both specular reflection light of illumination light and scattered/diffracted light thereof by using an objective lens. Meanwhile, the dark-field illumination scheme is a scheme which, without taking in the specular reflection light, takes in only the scattered/diffracted light by using the objective lens. In general, the bright-field illumination scheme is superior in the defect detection sensitivity; whereas the dark-field illumination scheme is suitable for speeding up the inspection speed. As a result, in many cases, the bright-field illumination scheme is mainly used for inspecting more microscopic defects; whereas the dark-field illumination scheme is used for high-speed 100-% inspection. Incidentally, in the high-speed 100-% inspection, a higher priority is given to the processing speed rather than to the highest sensitivity. In recent years, however, the defects to be inspected have become more and more microscopic in accompaniment with the enhancement in the integration scale of semiconductor devices. This situation has required that even higher performance for the microscope optics be implemented in defect inspection apparatuses of the bright-field illumination scheme as well.

Resolving power of an optical microscope is determined in principle by wavelength of light to be used for image-formation and numerical aperture (NA) of an objective lens. Accordingly, so far, higher-performance implementation for the optical microscope has been accomplished as the higher resolving-power implementation based on shorter-wavelength implementation for the wavelength of light to be used for image-formation and higher numerical-aperture (NA) implementation for the objective lens. These implementations enhance the resolving power of the optical microscope, thereby enhancing gray-scale contrast between both of microscopic patterns and microscopic defects existing thereon, and thus making it easier to detect more microscopic defects. In the status quo, however, the shortest wavelength of a light source usable for the optical microscope is equal to about 200 nm at best. Namely, there exists a limit to the enhancement in the resolving power which is based on the shorter-wavelength implementation. Also, as the numerical aperture (NA) of the objective lens, an objective lens whose numerical aperture is high enough, i.e., 0.8 to 0.9, has been already used in the bright-field illumination scheme. This high numerical-aperture value is substantially the limit as a dry-type objective lens. Moreover, even if an immersion-type objective lens is used together with a liquid whose refractive index is equal to 1 or more, the numerical-aperture value capable of being implemented is equal to about 1.5 at the maximum. Consequently, the enhancement in the resolving power remains at only about 1.6 times larger as compared with the case of the dry-type objective lens at present.

In view of this situation, as a technology for enhancing the resolving power by using a method other than the shorter-wavelength implementation for the light source and the increase in the objective-lens numerical aperture, there exists a method of using the super-resolution technology as disclosed in JP-A-2000-155099. Spatial frequency itself for the resolution limit is determined by the wavelength to be used and the objective-lens numerical aperture. Accordingly, this method cannot improve the spatial frequency itself for the resolution limit. Instead, this method suppresses low spatial-frequency band in the transfer function (MTF) of the image-formation system, and lifts up the high spatial-frequency band relatively. This operation enhances the gray-scale contrast between both of the microscopic patterns and the microscopic defects existing thereon, thereby making it easier to detect more microscopic defects.

In the defect detection using an imaging device, a light-amount range which the imaging device is capable of detecting, i.e., the dynamic range, is finite. As a result, the defect detection capability is generally determined by gray-scale contrast of the ratio between a light-amount difference caused to occur on the image at a defect position by the presence or absence of the defect, and a light amount at which output signals from the imaging device become saturated. The methods explained in the conventional embodiments, i.e., the shorter-wavelength implementation for the light source, the increase in the objective-lens numerical aperture, and the super-resolution technology, enhance the gray-scale contrast between both of the microscopic patterns and the microscopic defects existing thereon, thereby making it easier to detect more microscopic defects. These methods have found it possible to enhance the detection sensitivity for the microscopic defects because of the following reason: Namely, when an optical-microscope image of an inspection-target object is acquired, if low spatial-frequency structures on the inspection-target object, such as a non-pattern portion and a wide-area pattern portion, have become the brightest portions on the optical-microscope image, the gray-scale contrast of the microscopic defects will be enhanced while the brightness of the low spatial-frequency structures will be suppressed relatively. However, if the microscopic patterns, which are also high spatial-frequency structures as is the case with the microscopic defects, have become the brightest portions, the gray-scale contrast of the microscopic defects will be enhanced. At the same time, however, the gray-scale contrast of the microscopic patterns will also be enhanced simultaneously. Consequently, there has existed a problem that it is impossible to enhance the detection sensitivity for the microscopic defects further than that.

SUMMARY OF THE INVENTION

It is an object of the present invention to provide a semiconductor defect inspection apparatus which allows implementation of the high detection sensitivity for the microscopic defects even when the light-source wavelength and objective-lens numerical aperture remain the same.

The configurations of the present invention for accomplishing the above-described object are as follows:

A defect inspection apparatus including an illuminating unit for irradiating an inspection-target object with light, an image forming unit for forming an image of the light reflected by the inspection-target object, an imaging unit for imaging the image formed by the image forming unit, a defect detecting unit for detecting a defect on the inspection-target object on the basis of a picture acquired by the imaging unit, and a light shielding unit for permitting the light from the illuminating unit to pass through the light shielding unit, and irradiating the inspection-target object with the light, the light shielding unit including a mechanism which allows switching of pattern configuration of a light shielding portion.

As the inspection-target object, although semiconductor wafer and liquid-crystal display panel are the representative ones, the inspection-target object is not limited thereto. Namely, whatever objects are allowable as long as they suffer from the problem that defects exist on the surface and foreign substances adhere onto the surface. As the light source, whatever light sources are applicable, such as incoherent light from halogen lamp or the like and coherent light from laser or the like. As the imaging unit, although two-dimensional CCD, CMOS sensor, and TDI, i.e., high-speed line sensor, are the representative ones, whatever units are allowable as long as they are capable of recording the images as electronic data.

According to the present invention, it becomes possible to illuminate an inspection-target object at only an incident angle at which the gray-scale contrast of the microscopic defects will be emphasized more sharply. This characteristic allows the gray-scale contrast of the microscopic defects to be emphasized more sharply than the gray-scale contrast of the microscopic patterns, thereby making it possible to detect the microscopic defects with a high sensitivity.

Other objects, features and advantages of the invention will become apparent from the following description of the embodiments of the invention taken in conjunction with the accompanying drawings.

DESCRIPTION OF THE INVENTION

The present invention takes advantage of the following phenomenon: Namely, when the incident angle of an illumination light beam onto an inspection-target object surface is varied, the gray-scale contrast of the microscopic patterns and the gray-scale contrast of the microscopic defects within a microscope image exhibit mutually different variations. Accordingly, the present invention is configured to illuminate the inspection-target object at only an incident angle at which the gray-scale contrast of the microscopic defects will be emphasized more sharply. Hereinafter, the detailed explanation will be given below concerning the present invention.

Figure 8:
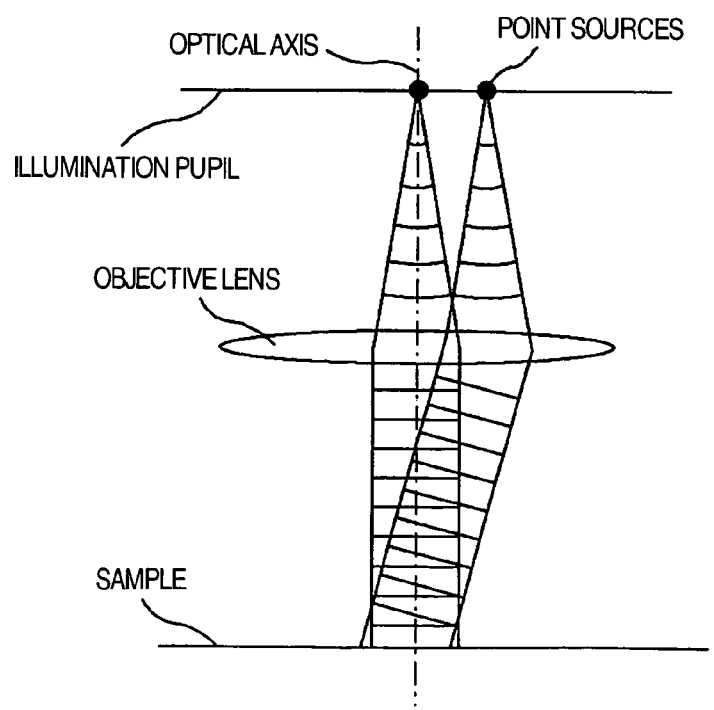
FIG. 8 is a diagram for illustrating relationship between incident angle of illumination light and illumination pupil.

In microscope optics, at what incident angle an illumination light beam will be irradiated onto a sample is determined by which of positions on an illumination pupil this illumination light beam has passed through. FIG. 8 illustrates this situation in the two-dimensional case. An illumination light beam, which has passed through center of the optical axis, performs normal incidence into the sample surface which is located normally to the optical axis. An illumination light beam, which has passed through a portion positioned nearer to the outer circumference of the illumination pupil within the range of the illumination pupil, performs oblique incidence into the sample surface at a large incident angle. In general, optical microscopes use incoherent illumination, where all of illumination light beams passing through the entire plane of the illumination pupil are used for image-formation, or partial coherent illumination, where only illumination light beams passing through the inner-circumference plane of the illumination pupil excluding the outer-circumference portion thereof are used therefor. The illumination where only an illumination light beam passing through exactly a single point on the illumination pupil is used therefor is referred to as coherent illumination. In the coherent illumination, the sample surface is illuminated with the illumination light beam which has exactly a single incident angle. In the incoherent illumination/partial coherent illumination, the sample surface is illuminated with the illumination light beams where various incident angles are mixed. In these illuminations, it is conceivable that the illumination light beam passing through a single point on the illumination pupil is equivalent to a state where a single point source is located at the pass-through position on the illumination pupil. At this time, it turns out that the partial coherent illumination is equivalent to a state where point sources are located at all of the positions within an inner circumference of a certain radius on the illumination pupil. On account of this, the intensity distribution of an image-formed picture created based on the partial coherent illumination is equal to an intensity distribution resulting from integrating all of intensity distributions of image-formed pictures created by the respective point sources based on the coherent illumination.

Figure 9:
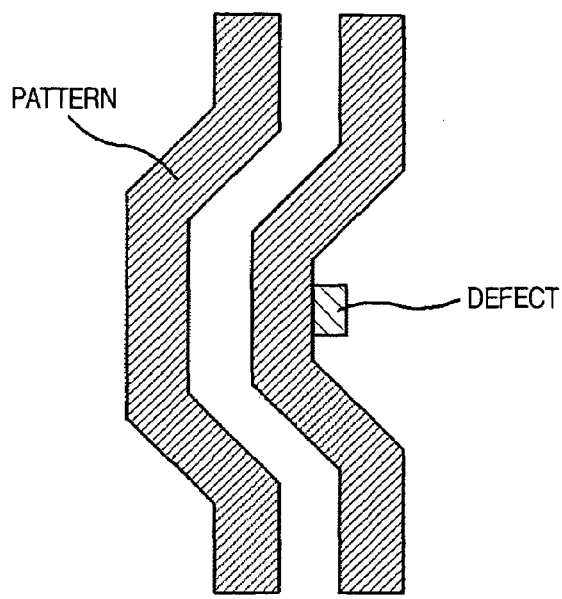
FIG. 9 illustrates an example of a pattern and a defect formed on a semiconductor wafer.
Figure 10:
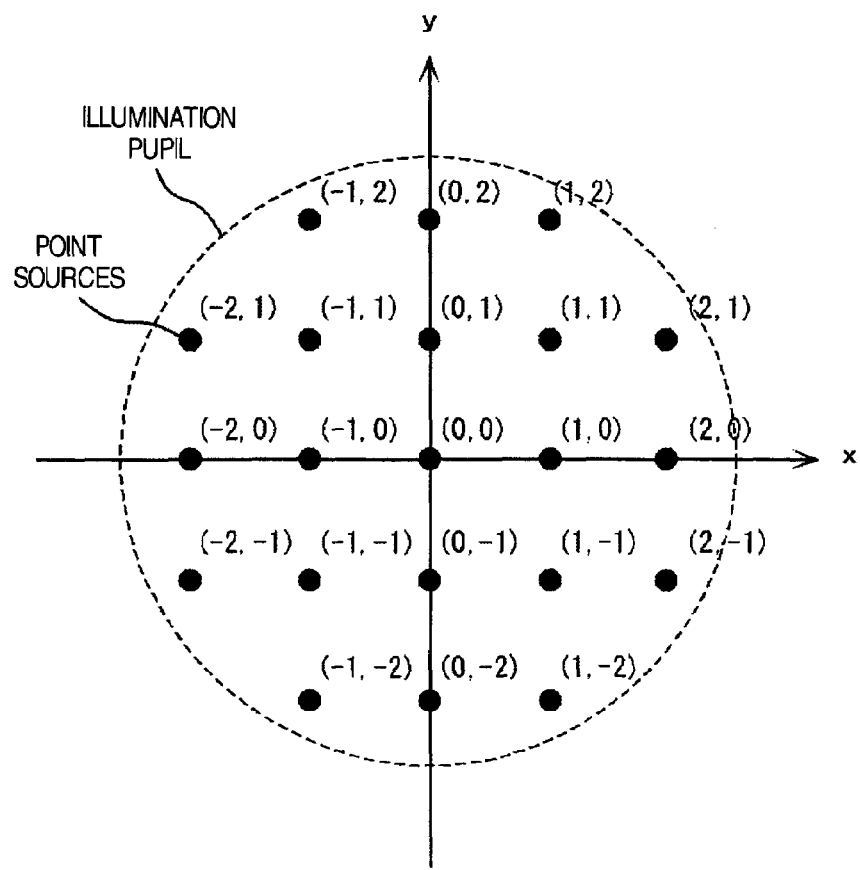
FIG. 10 is a diagram for illustrating placement of point light-sources on the illumination pupil.
Figure 11:
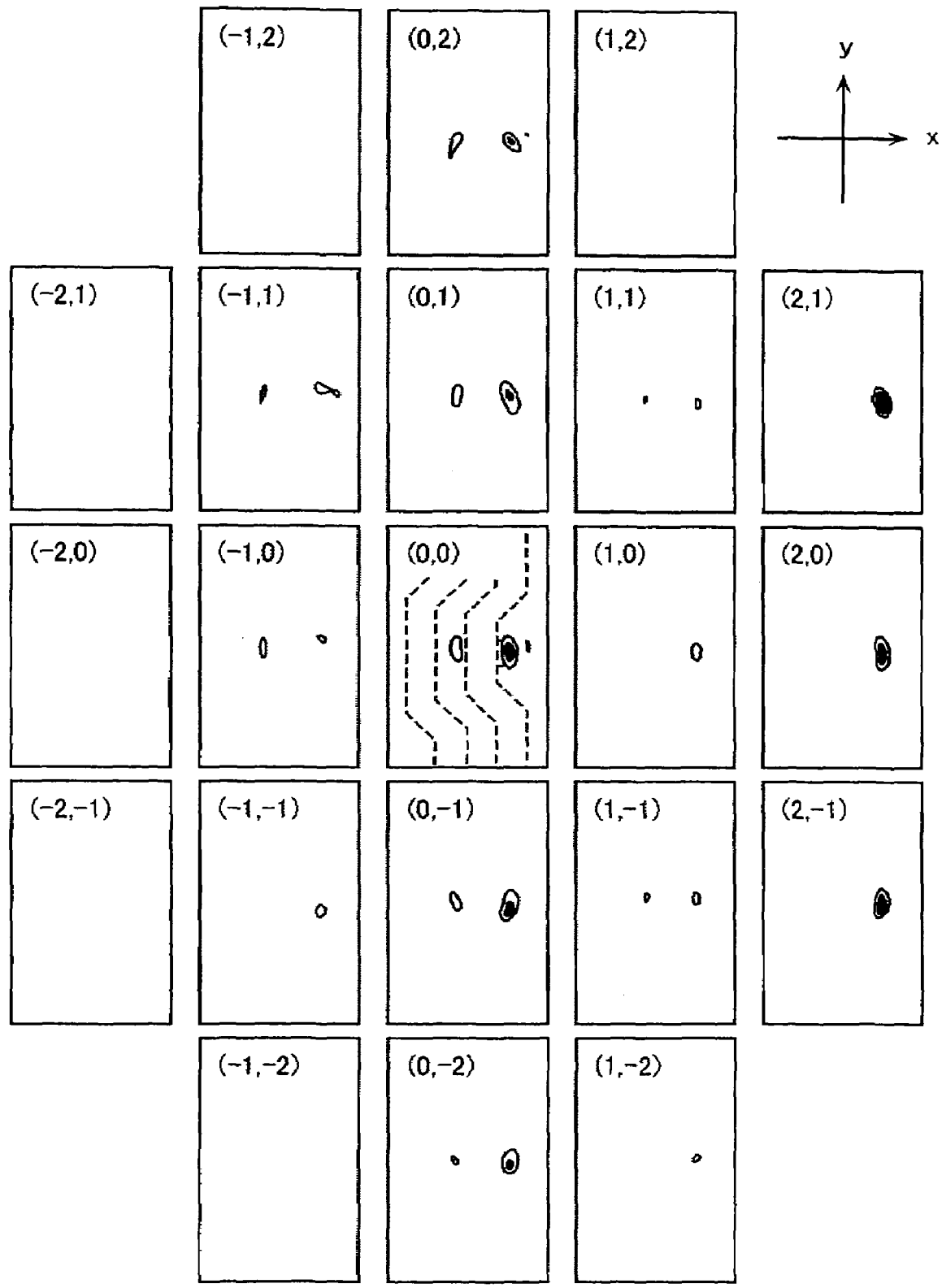
FIG. 11 is a diagram for illustrating differences in the microscopic-defects contrast due to differences in the incident angle.

Here, assume a case of selecting a sample where a pattern as illustrated in FIG. 9 is formed on a semiconductor wafer, and where a microscopic defect is contained in part of this pattern. In this case, the following problem has been analyzed and inspected based on an optical simulation using the finite difference time domain method (FDTD): Namely, how the image-formed picture on the periphery of the microscopic defect based on the coherent illumination will be varied depending on differences in the position at which an illumination light beam has passed through the illumination pupil, i.e., differences in the incident angle with respect to the sample surface. FIG. 10 and FIG. 11 illustrate a result obtained by this optical simulation analysis. In FIG. 11, image-formed results acquired by respective twenty-one light-sources placed on the illumination pupil as are illustrated in FIG. 10 are arranged in the same placement. FIG. 11 displays images created by subtracting the images with none of the microscopic defect from the images with the microscopic defect. This is performed in order that differences in the images due to the presence or absence of the microscopic defect become easy to understand. FIG. 11 indicates that there exist locations where the signal intensity difference between two images of the presence/absence of the microscopic defect at the position of the microscopic defect is larger or smaller depending on the differences in the incident angle. This indication further indicates that, by illuminating the sample at only an incident angle at which the signal intensity difference between the two images of the presence/absence of the microscopic defect at the position of the microscopic defect will become larger, only the microscopic defect can be detected by being effectively emphasized. In this way, illuminating the sample at only the incident angle at which the signal intensity difference between the two images of the presence/absence of the microscopic defect at the position of the microscopic defect will become larger can be implemented as follows: Namely, the light is permitted to transmit only a position on the illumination pupil which corresponds to such an incident angle, and light-shielding is imposed on the other portion so that the light is not permitted to transmit the other portion.

Hereinafter, the explanation will be given below concerning embodiments of the present invention.

EMBODIMENT 1

Figure 1:
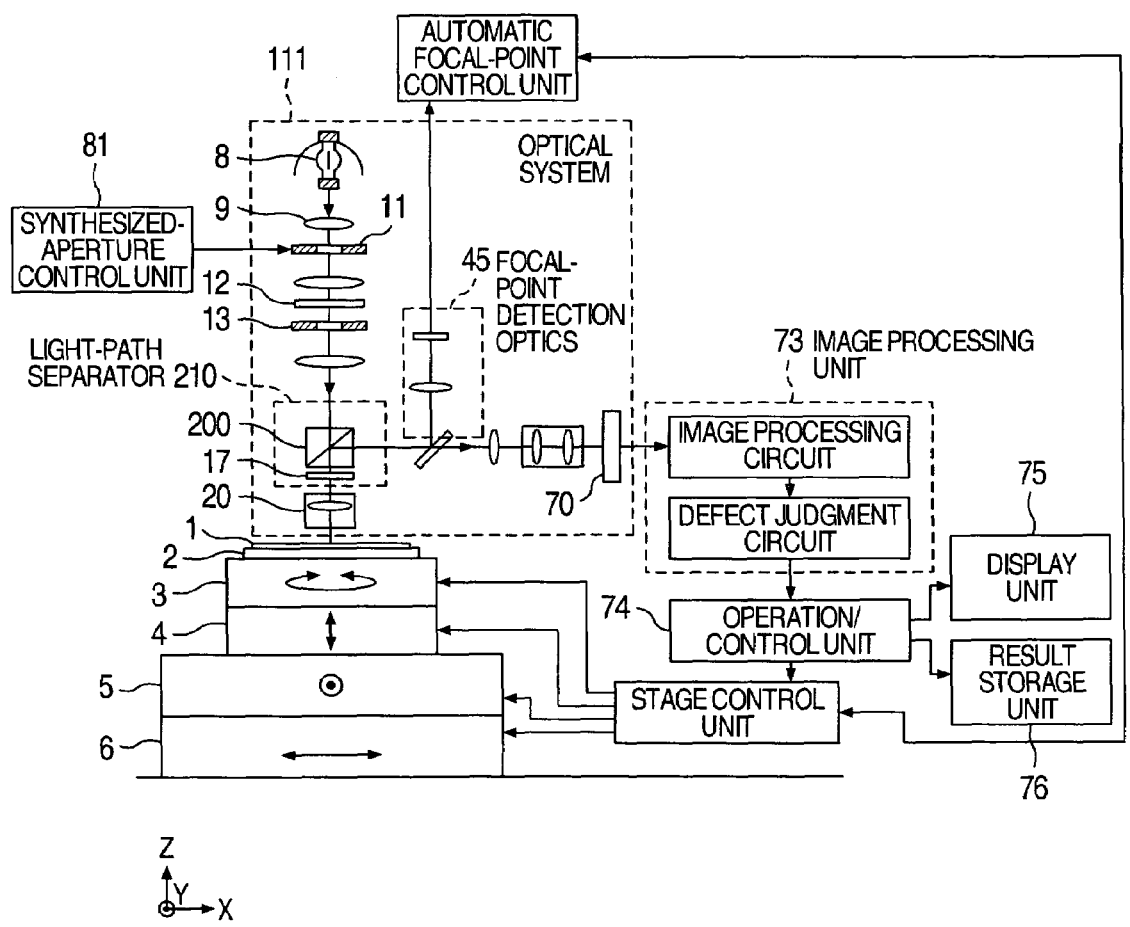
FIG. 1 illustrates an embodiment of the defect inspection apparatus according to the present invention.

FIG. 1 illustrates an embodiment of the optical defect inspection apparatus using a microscopic-defect detection method according to the present invention. A semiconductor wafer 1, which is an inspection-target object, adheres to a wafer chuck 2 through vacuum absorption. This wafer chuck 2 is mounted on a O stage 3, a Z stage 4, a Y stage 5, and an X stage 6. An optics 111 located above the semiconductor wafer 1 photographs an optical image of the semiconductor wafer 1 in order to perform defect inspection of patterns formed on the semiconductor wafer 1. The optics 111 mainly includes an illumination optics, an image-formation optics for creating and imaging the image of the semiconductor wafer 1, and a focal-point detection optics 45. A light-source 8 located in the illumination optics is an incoherent light-source, which is, e.g., a xenon lamp.

Light emitted from the light-source 8 passes through an aperture portion of an aperture stop 11 located on an illumination pupil via a lens 9, then attaining to a field stop 13 via a lens and a wavelength selection filter 12. Taking spectral reflectance of the semiconductor wafer 1 into consideration, this wavelength selection filter 12 limits illumination wavelength band in order to detect the high-resolution image of the semiconductor wafer 1. As the wavelength selection filter 12, an interference filter is located for example. The light which has passed through the field stop 13 performs incidence into a light-path separator 210.

In the light-path separator 210, a polarization beam splitter 200 is used for guiding illumination light-amount to the image-formation optics with a high efficiency. The light-path separator 210 makes the separation between the light path of the illumination light traveling from the light-source 8 to the semiconductor wafer 1 and a light path of the illumination light traveling from the semiconductor wafer 1 to an imaging device 70. The illumination light (randomly-polarized light) which has performed incidence into the light-path separator 210 passes through the polarization beam splitter 200, thereby becoming p-polarization linearly-polarized light. After that, the p-polarization linearly-polarized light passes through a quarter-wave plate 17, thereby becoming circularly-polarized light, and then being irradiated onto the semiconductor wafer 1 via an objective lens 20. The light illuminated onto the semiconductor wafer 1 is reflected, scattered, and diffracted on the semiconductor wafer 1. Then, the light whose divergence falls within the NA of the objective lens 20 performs incidence into the objective lens 20 once again, then passing through the quarter-wave plate 17. Here, part (part of the high-order diffracted light) of the light reflected by the semiconductor wafer 1 becomes circularly-polarized light whose rotation direction will not change at the time of the reflection. Then, the circularly-polarized light becomes p-polarization linearly-polarized light when it passes through the one-quarter wavelength plate 17 once again. Most of the light reflected by the semiconductor wafer 1, however, becomes circularly-polarized light whose rotation direction becomes inverted at the time of the reflection. Then, the circularly-polarized light becomes s-polarization linearly-polarized light when it passes through the one-quarter wavelength plate 17 once again. On account of this, in the polarization beam splitter 200, only the latter (i.e., the s-polarization linearly-polarized light) is reflected with almost no loss inflicted thereon, thereby being guided to the image-formation optics with a high efficiency. This allows the image of the semiconductor wafer 1 to be formed on the imaging device 70. This image is converted into an electrical signal, then being taken into an image processing unit 73. The image processing unit 73 detects a defect by making the comparison between a detected image and a reference image. Here, the detected image is acquired by scanning the patterns having the same configuration and arranged continuously with an equal spacing in the row/column directions on the semiconductor wafer 1. The reference image is acquired by scanning patterns having the same configuration and being adjacent thereto in the row/column directions.

An operation/control unit 74 controls the 9 stage 3, the Z stage 4, the Y stage 5, and the X stage 6, the illumination optics, the image-formation optics, the focal-point detection optics 45, and the image processing unit 73. Namely, while scanning the inspection area on the semiconductor wafer 1, the operation/control unit 74 takes in the defect detection result from the image processing unit 73, then displaying the result on a display unit 75, and storing the result into a result storage unit 76.

Figure 2:
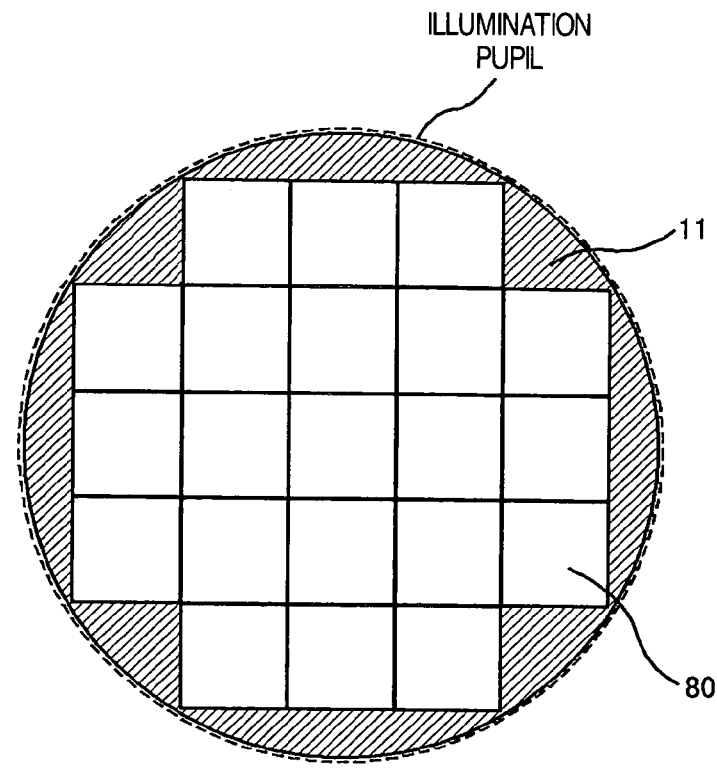
FIG. 2 illustrates a configuration example 1 of aperture stop in the embodiment of the defect inspection apparatus according to the present invention.

Here, the above-described aperture stop 11 is divided into twenty-one square-shaped small apertures 80 as is illustrated in FIG. 2. Each small aperture includes one optical switch. Accordingly, based on an open/close electrical signal from a synthesized-aperture control unit 81, each small aperture is capable of being switched between an "open" state where light is permitted to transmit each small aperture and a "close" state where light is not permitted to transmit each small aperture. The synthesized-aperture control unit 81 is capable of opening/closing each of the twenty-one small apertures independently of each other. Also, the synthesized-aperture control unit 81 allows "a combined aperture", which is formed of an assembly of the small apertures lying in the "open" state, to be created in an arbitrary combination of these small apertures. Of the light emitted from the light-source 8, only the light which has passed through this combined aperture becomes the illumination light, thereby being irradiated onto the semiconductor wafer 1. It is desirable to determine the combination for this combined aperture such that defect contrast will become substantially maximized. This determination is performed while maintaining the entire illumination light-amount capable of passing through the illumination pupil plane so that the light-amount will become larger than a constant value. Here, the above-described defect contrast is defined as a ratio of the absolute value of a signal intensity difference with respect to the signal intensity of the brightest portion on the reference image, the signal intensity difference being calculated between the detected image and the reference image at the position of a microscopic defect to be detected. For this purpose, as described above, the operation/control unit 74 installs therein a synthesized-aperture determination function which includes the steps described below:

step 1: The semiconductor wafer 1, which is to be used for the synthesized-aperture determination, and which contains an evaluation-target defect, is introduced into the defect inspection apparatus, then being fixed on the wafer chuck 2.

step 2: All of the above-described twenty-one small apertures 80 are switched sequentially, thereby setting only one of the twenty-one small apertures into the "open" state, and setting all the remaining twenty small apertures into the "close" state. Then, the following steps 3 to 4 will be repeated.

step 3: Based on "coordinate value of the evaluation-target defect" inputted from the operator, a detected image and a reference image are taken in. Here, the detected image is acquired by scanning a pattern containing the specified defect out of patterns having the same configuration and arranged continuously with an equal spacing in the row/column directions on the semiconductor wafer 1. The reference image is acquired by scanning a pattern containing none of defects having the same configuration and being adjacent thereto in the row/column directions.

step 4: From brightness of the detected image at the specified defect coordinate position, brightness of the reference image at a position corresponding to the specified defect coordinate position is subtracted. Then, the value acquired by this subtraction is saved as "a defect-signal intensity difference" of the small aperture which lies in the "open" state at that time.

step 5: Of twenty-one "defect-signal intensity differences" acquired by the repetition of the steps 3 to 4, total of absolute values of the "defect-signal intensity differences" having positive sign and total of absolute values of the "defect-signal intensity differences" having negative sign are calculated.

step 6: In the result acquired at the step 5, if the total of the absolute values of the "defect-signal intensity differences" having positive sign is found to be larger, the twenty-one "defect-signal intensity differences" are rearranged in the descending order with the signs. Meanwhile, if the total of the absolute values of the "defect-signal intensity differences" having negative sign is found to be larger, the twenty-one "defect-signal intensity differences" are rearranged in the ascending order with the signs.

step 7: In accordance with "the number of the small apertures which should be set into the "open" state as the combined aperture" inputted from the operator, combination of the small apertures to be set into the "open" state is determined in the order of the "defect-signal intensity differences" rearranged at the step 6.

With respect to a defect which is of the same type as the evaluation-target defect at the time of the synthesized-aperture determination, the defect inspection is performed by illuminating the semiconductor wafer 1 with the use of the combined aperture determined in this way. This method allows the defect contrast to become substantially maximized even if the microscopic pattern, which is also a high spatial-frequency structure as is the case with the microscopic defect, has become the brightest portion on the detected image and the reference image. Consequently, it becomes possible to perform the inspection in a state where the detection sensitivity has been optimized.

Incidentally, at the above-described step 2, the number of the small apertures to be set into the "open" state has been determined on the one-by-one basis. However, If the use of only one small aperture results in a shortage of the illumination light-amount, and thus makes it impossible to measure the "defect-signal intensity differences" correctly, it is also allowable to combine a plurality of adjacent small apertures, and to evaluate the combined small apertures as the "open" states simultaneously.

Figure 3A:
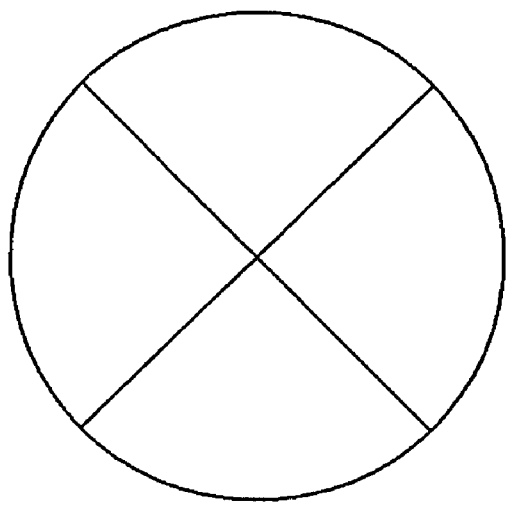
FIG. 3A to FIG. 3C illustrate a configuration example 2 of the aperture stop in the embodiment of the defect inspection apparatus according to the present invention.
Figure 3B:
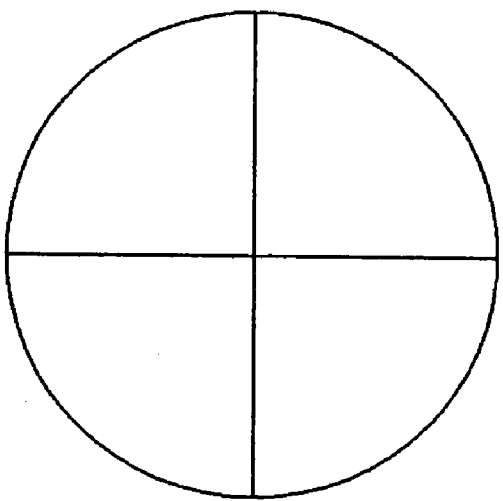
Figure 3C:
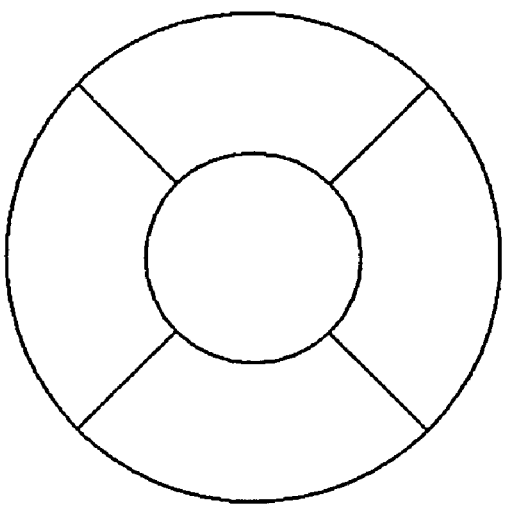

The division number of the above-described aperture stop 11 into the small apertures 80 has been defined as being twenty one. The degree of freedom of the combination, however, increases as the division number becomes larger. Accordingly, the division number may be larger than twenty one. If the division number is sufficiently large enough, it is needless to say that, from the manufacturing/control point-of-view, it is advantageous to make configurations of the respective small apertures as the same configuration as possible, and to locate the small apertures with an equal spacing and without clearance in the transverse and longitudinal directions. Concerning the case of the smaller division number, many of the patterns formed on the semiconductor wafer 1 extend in a line-like manner in the transverse and longitudinal directions. This situation requires that incident angles from at least up-and-down and right-to-left directions be implemented with respect to those patterns. Consequently, it is desirable to make the four or more divisions of configurations illustrated in FIG. 3A and FIG. 3B. Moreover, it can easily be estimated that the illumination light which performs the normal incidence into the surface of the semiconductor wafer 1 exhibits different properties regarding the defect contrast in comparison with the case of the oblique incidence. Accordingly, it is also desirable to form the central portion of the illumination pupil into an independent small aperture as is illustrated in FIG. 3C.

Figure 4A:
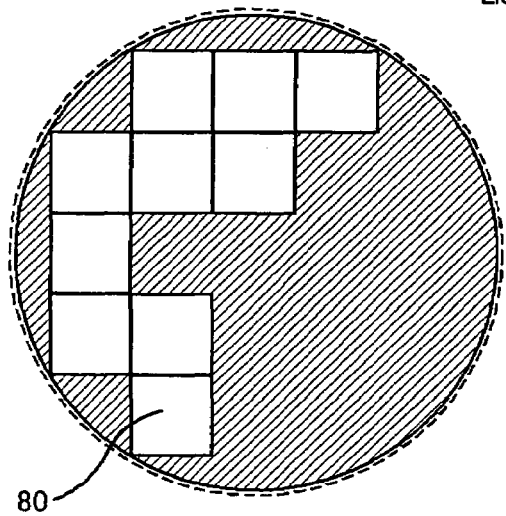
FIG. 4A to FIG. 4D illustrate a configuration example 3 of the aperture stop in the embodiment of the defect inspection apparatus according to the present invention.
Figure 4B:
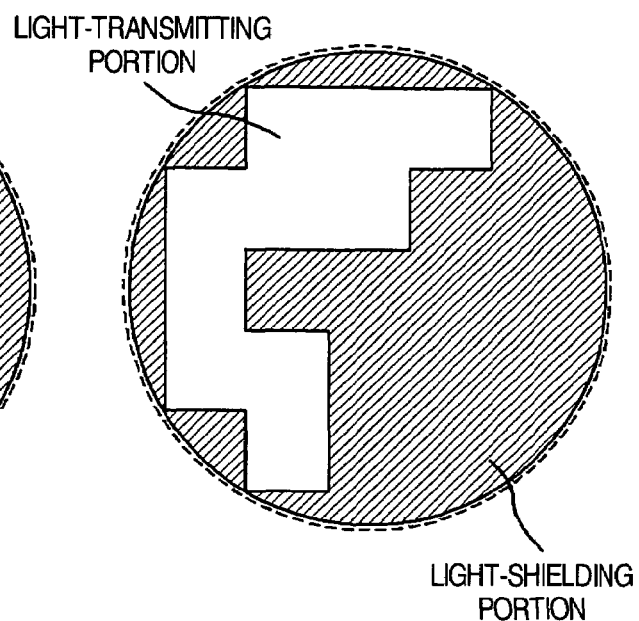
Figure 4C:
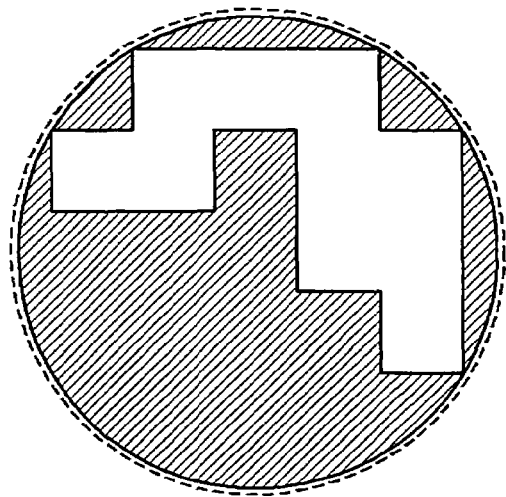

Also, assume that the combination for the combined aperture determined by the synthesized-aperture determination function in the above-described embodiment is a combination as illustrated in FIG. 4A. At this time, this case is equivalent to a state where a light-shielding plate of the configuration in FIG. 4B is located as an aperture stop on the illumination-pupil position. Accordingly, instead of configuring the aperture stop with the use of a plurality of small apertures whose light-shield/light-transmission can be arbitrarily switched as in the above-described embodiment, the switching may also be performed by preparing in advance necessary combination's number of aperture stops of fixed configurations like this. However, if the division number into the small apertures is large, tremendously large number of combinations become necessary. For example, assuming that the number of the small apertures in the "open" state necessary for ensuring the illumination light-amount is equal to ten of the twenty-one small apertures as in the above-described embodiment, acquiring the same effect requires preparation of light-shielding plates the number of whose types is equal to $$_{21}C_{10} = 352,716,$$

which is not a realistically applicable number. However, if the division number into the small apertures is small, e.g., if the aperture stop is divided into the small apertures as is illustrated in FIG. 3C, and if the number of the small apertures in the "open" state necessary for ensuring the illumination light-amount is equal to two, acquiring the same effect requires preparation of light-shielding plates the number of whose types is equal to only $$_5C_2=10,$$

which is a realistically applicable number. Furthermore, there is provided in advance a unit for making it possible to displace the position of a selected light-shielding plate in such a manner as the parallel displacement in the transverse and longitudinal directions on the illumination pupil, or as the rotation with respect to the optical axis, or as a combination of the parallel displacement and the rotation. This unit makes it possible to implement the light-shielding plate of the configuration in FIG. 4B and the light-shielding plate of the configuration in FIG. 4C by rotating one and the same light-shielding plate. Consequently, it becomes possible to reduce the types of the light-shielding plates which must be prepared in advance.

Figure 5:
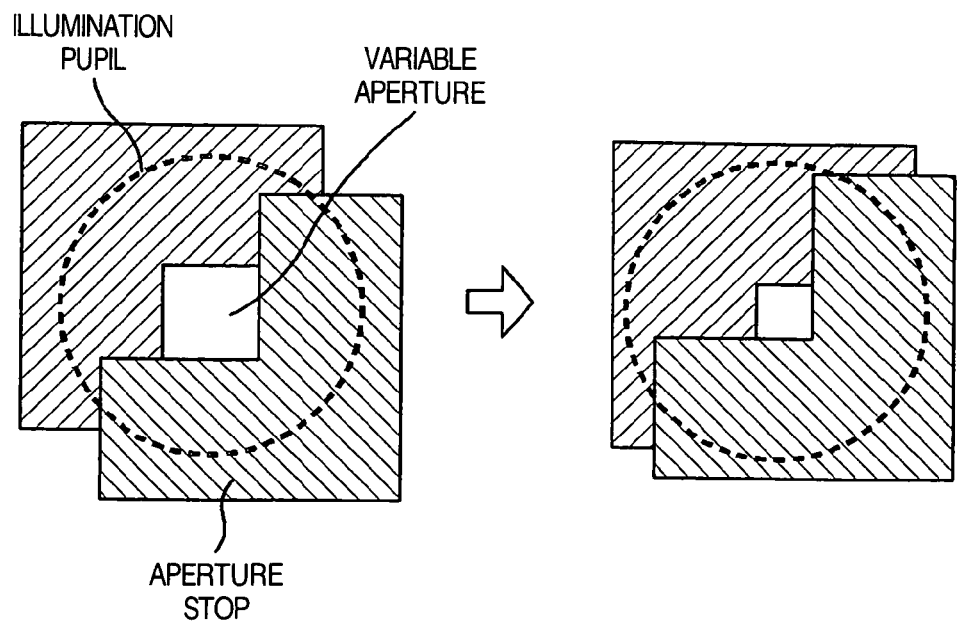
FIG. 5 illustrates a configuration example 4 of the aperture stop in the embodiment of the defect inspection apparatus according to the present invention.
Figure 4D:
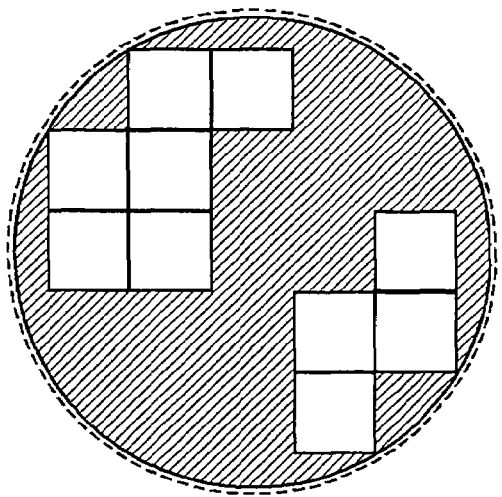

Also, as another alternative proposal which can be implemented more simply, and which can acquire basically the same effect although it cannot acquire completely the same effect as the one in the above-described embodiment, the following technology is possible: Namely, as illustrated in FIG. 5, an aperture stop which is capable of making its aperture size variable is located on the illumination pupil such that the parallel displacement of the aperture stop is made executable in the transverse and longitudinal directions. In this alternative proposal, if the configuration of the combined aperture determined in the above-described embodiment is not a simple convex polygon as in FIG. 4A, or if the aperture portion is divided into discontinuous two or more areas as in FIG. 4D, the same aperture configurations cannot be implemented. Nevertheless, if the combined aperture can be approximated by the aperture configuration of the aperture stop, basically the same effect can be acquired.

EMBODIMENT 2

Figure 6:
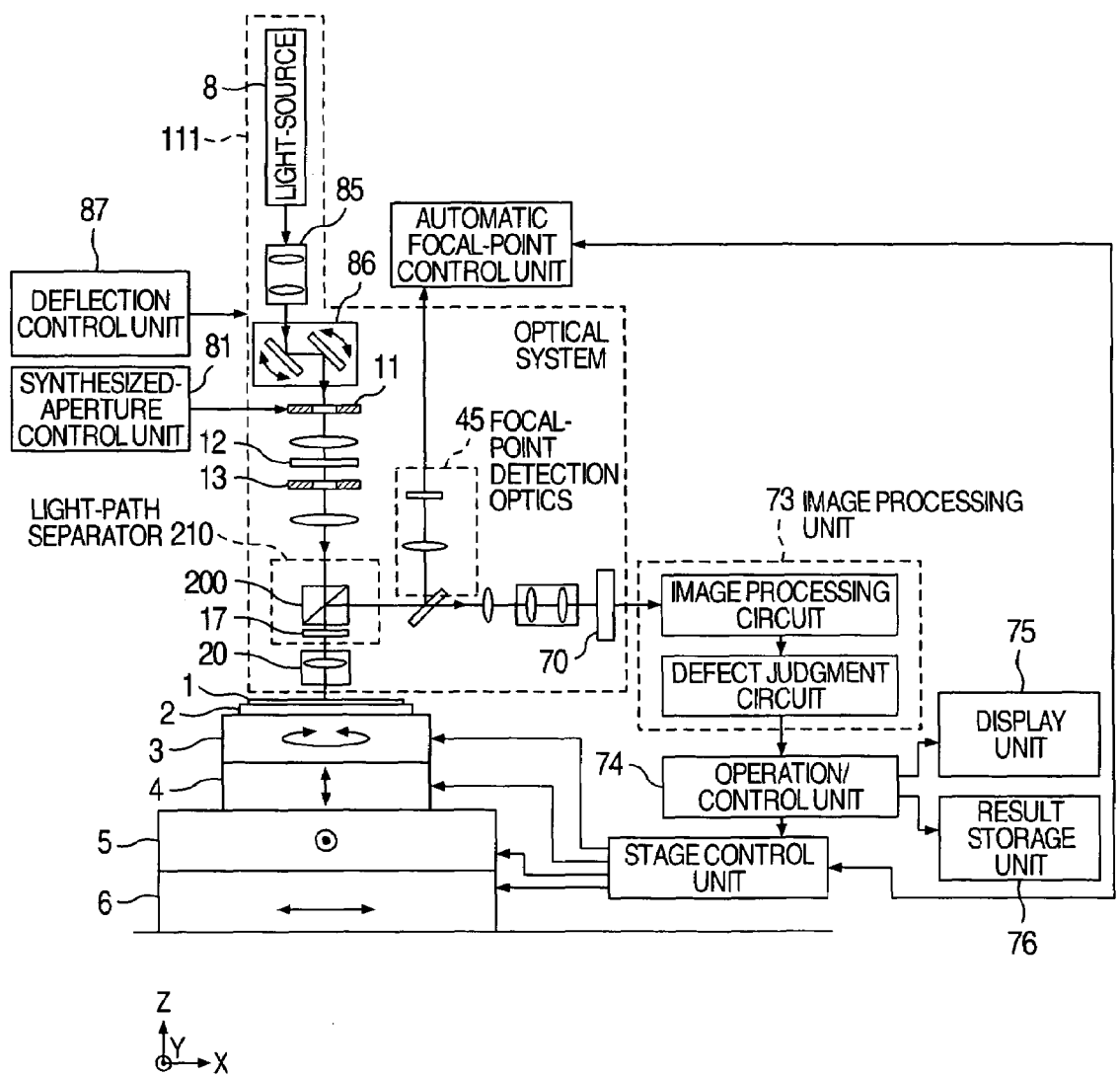
FIG. 6 illustrates another embodiment of the defect inspection apparatus according to the present invention.

Next, FIG. 6 illustrates another embodiment of the optical defect inspection apparatus using the microscopic-defect detection method according to the present invention. Except the configurations of the light-source and the illumination optics, the other configurations are in common with the first embodiment illustrated in FIG. 1. Accordingly, the explanation about the other configurations will be omitted. In the present embodiment, the light-source 8 located in the illumination optics is a laser light-source.

Figure 7:
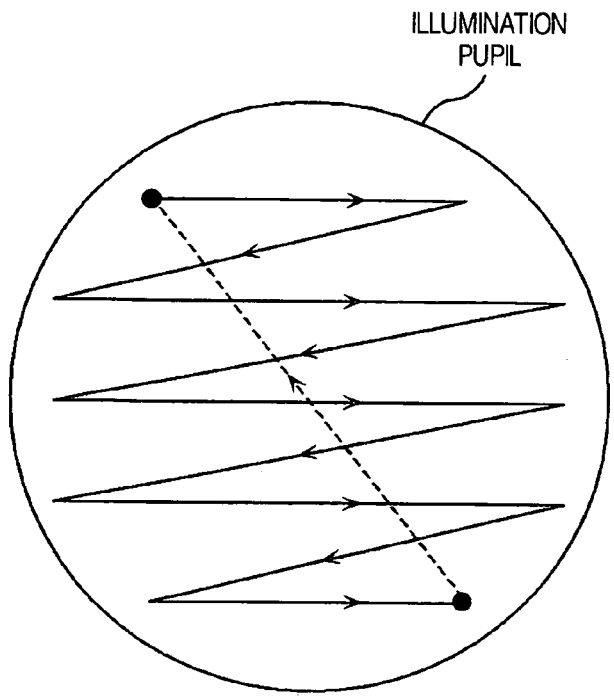
FIG. 7 illustrates details of laser-beam scanning in another embodiment of the defect inspection apparatus according to the present invention.

Light emitted from the light-source 8 is shaped by a beam shaper 85 in its beam cross-section configuration. Even after the shaping, cross-section area of the laser beam is smaller than the illumination pupil. This laser beam performs incidence into a light-flux fluctuation system 86. Based on an instruction from a deflection control unit 87, the light-flux fluctuation system 86 is capable of deflecting the laser beam so that the laser beam will pass through an arbitrary position on the illumination pupil. Moreover, the system 86 is capable of exercising the scanning control by oscillating the deflection position in terms of time. Usually, it is repeated that the laser beam is deflected in terms of time as is illustrated in FIG. 7 such that the area to be scanned will cover the entire plane of the illumination pupil. It is possible, however, to cause only a necessary partial area to be scanned. As is the case with the first embodiment illustrated in FIG. 1, the laser beam which has passed through the illumination pupil illuminates the semiconductor wafer 1, then traveling to the image-formation optics.

In the present embodiment, the scanning with the laser beam is performed within only the area which has been set as the aperture portion of the combined aperture determined in the first embodiment illustrated in FIG. 1. This scanning makes it possible to acquire the same effect as the one which has been implemented by locating the plurality of divided small apertures on the illumination pupil plane in the embodiment illustrated in FIG. 1.

Also, in the present embodiment as well, the operation/control unit 74 installs therein the synthesized-aperture determination function. Its processing contents and steps are the same as those in the embodiment illustrated in FIG. 1. According to the present embodiment, with respect to a defect which is of the same type as the evaluation-target defect at the time of the synthesized-aperture determination, the defect inspection is performed by illuminating the semiconductor wafer 1 with the use of the combined aperture determined in this way. This method allows the defect contrast to become substantially maximized even if the microscopic pattern, which is also a high spatial-frequency structure as is the case with the microscopic defect, has become the brightest portion on the detected image and the reference image. Consequently, it becomes possible to perform the inspection in a state where the detection sensitivity has been optimized.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A defect inspection apparatus, comprising:
   illuminating means for irradiating an inspection-target object with light;
   image forming means for forming an image of said light reflected by said inspection-target object;
   imaging means for imaging said image formed by said image forming means;
   defect detecting means for detecting a defect on said inspection-target object on the basis of a picture acquired by said imaging means; and
   light shielding means for permitting said light from said illuminating means to pass through said light shielding means, and irradiating said inspection-target object with said light, said light shielding means including a mechanism which allows switching of pattern configuration of a light shielding portion,
   wherein said light shielding means is means for dividing a light-transmission plane into a plurality of small apertures, and switching light-shield/light-transmission for said small apertures.

2. The defect inspection apparatus according to claim 1, wherein said small apertures have substantially the same configuration.

3. The defect inspection apparatus according to claim 1, wherein said plurality of small apertures include
   one circular or polygonal small aperture located at substantially the center of said light-transmission plane, or apertures acquired by further dividing said small aperture into a plurality of small apertures; and
   apertures acquired by dividing an external portion of said small aperture or said apertures in a radial manner.

4. The defect inspection apparatus according to claim 3, further comprising:

switching means for switching said light-shield/light-transmission for said small apertures on one small-aperture basis or with two or more small apertures regarded as one group.

5. The defect inspection apparatus according to claim 4, further comprising:
   defect-contrast measuring means for measuring defect contrast of a microscopic defect, said defect contrast being defined as a ratio of absolute value of a signal intensity difference with respect to signal intensity of the brightest portion on a reference image, said signal intensity difference being calculated between a detected image and said reference image at position of said microscopic defect to be detected; and
   control means for controlling pattern of a combined aperture so that said defect contrast will become substantially maximized, said combined aperture being formed of said small apertures in said light-transmission state, said control being performed based on a measurement result by said defect-contrast measuring means and while maintaining entire illumination light-amount capable of passing through said illumination pupil plane more largely than a constant value.

6. The defect inspection apparatus according to claim 5, further comprising:
   control means for measuring said signal intensity difference with a sign affixed thereto when measuring said detected image and said reference image by said defect-contrast measuring means, and determining said pattern of said combined aperture so that said defect contrast will become substantially maximized in a combination of said signal intensity differences whose affixed signs become one and the same sign, said combined aperture being formed of said small apertures in said light-transmission state.

7. The defect inspection apparatus according to claim 1, wherein each of said small apertures includes an optical switch, each of said small apertures being configured such that said light-shield/light-transmission for each of said small apertures is capable of being controlled using an electrical signal.

8. A pattern-defect inspection method, comprising:
   illuminating means for irradiating an inspection-target object surface with illumination light via an objective lens;
   image forming means for converging said illumination light by said objective lens again, and forming an image of said illumination light, said illumination light being reflected, scattered, and diffracted by said inspection-target object; and
   means for making it possible to switch and thereby to load or unload a plurality of illumination apertures on an illumination pupil plane of said illuminating means, said plurality of illumination apertures having different configurations or aperture areas,
   said pattern-defect inspection method, comprising a step of:
   detecting a defect by making a comparison between a detected image and a reference image, said detected image being acquired with an imaging device by scanning patterns having the same configuration and arranged continuously with an equal spacing in row/column directions on said inspection-target object, said reference image being acquired with said imaging device by scanning patterns having the same configuration and being adjacent thereto in said row/column directions, wherein
   there is further provided means for
   switching said plurality of illumination apertures having said different configurations or aperture areas;
   measuring defect contrast which is defined as a ratio of absolute value of a signal intensity difference with respect to signal intensity of the brightest portion on said reference image, said signal intensity difference being calculated between said detected image and said reference image at position of said microscopic defect to be detected; and
   determining types of said illumination apertures so that said defect contrast will become substantially maximized;
   said pattern-defect inspection method, further comprising a step of:
   selecting said types of said illumination apertures in accordance with a result of said determination.

9. A pattern-defect inspection method, comprising:
   illuminating means for irradiating an inspection-target object surface with illumination light via an objective lens;
   image forming means for converging said illumination light by said objective lens again, and forming an image of said illumination light, said illumination light being reflected, scattered, and diffracted by said inspection-target object; and
   means for making it possible to switch and thereby to load or unload a plurality of illumination apertures on an illumination pupil plane of said illuminating means, said plurality of illumination apertures having different configurations or aperture areas,
   said pattern-defect inspection method, comprising a step of:
   detecting a defect by making a comparison between a detected image and a reference image, said detected image being acquired with an imaging device by scanning patterns having the same configuration and arranged continuously with an equal spacing in row/column directions on said inspection-target object, said reference image being acquired with said imaging device by scanning patterns having the same configuration and being adjacent thereto in said row/column directions, wherein
   there is further provided means for making it possible to displace position of a selected illumination aperture in such a manner as its parallel displacement within said illumination pupil plane, or as its rotation with respect to an optical axis, or as a combination of both of said parallel displacement and said rotation, said selected illumination aperture being inserted on said optical axis.

10. The microscopic-defect inspection method according to claim 9, wherein there is further provided means for
    selecting/switching said plurality of illumination apertures having said different configurations or aperture areas;
    displacing position of said selected illumination aperture in such a manner as its parallel displacement within said illumination pupil plane, or as its rotation with respect to an optical axis, or as a combination of both of said parallel displacement and said rotation;
    measuring defect contrast which is defined as a ratio of absolute value of a signal intensity difference with respect to signal intensity of the brightest portion on said reference image, said signal intensity difference being calculated between said detected image and said reference image at position of said microscopic defect to be detected; and determining type and position of said illumination aperture so that said defect contrast will become substantially maximized;

said pattern-defect inspection method, further comprising a step of:

selecting/switching said type of said illumination aperture and controlling said position of said selected illumination aperture in accordance with a result of said determination.

11. A pattern-defect inspection method, comprising:

illuminating means for irradiating an inspection-target object surface with illumination light via an objective lens;

image forming means for converging said illumination light by said objective lens again, and forming an image of said illumination light, said illumination light being reflected, scattered, and diffracted by said inspection-target object; and an aperture stop on an illumination pupil plane of said illuminating means, said aperture stop being capable of making its aperture size variable, said pattern-defect inspection method, comprising a step of:

detecting a defect by making a comparison between a detected image and a reference image, said detected image being acquired with an imaging device by scanning patterns having the same configuration and arranged continuously with an equal spacing in row/column directions on said inspection-target object, said reference image being acquired with said imaging device by scanning patterns having the same configuration and being adjacent thereto in said row/column directions, wherein there is further provided means for making it possible to displace position of said aperture stop in such a manner as its parallel displacement within said illumination pupil plane.

12. The microscopic-defect inspection method according to claim 11, wherein there is further provided means for changing said aperture size and position of said aperture stop;

measuring defect contrast which is defined as a ratio of absolute value of a signal intensity difference with respect to signal intensity of the brightest portion on said reference image, said signal intensity difference being calculated between said detected image and said reference image at position of said microscopic defect to be detected; and determining said aperture size and position of said aperture stop so that said defect contrast will become substantially maximized, said pattern-defect inspection method, further comprising a step of:

controlling said aperture size and position of said aperture stop in accordance with a result of said determination.

13. A pattern-defect inspection method, comprising:

illuminating means for irradiating an inspection-target object surface with illumination light via an objective lens, said illuminating means having a laser light-source;

image forming means for converging said illumination light by said objective lens again, and forming an image of said illumination light, said illumination light being reflected, scattered, and diffracted by said inspection-target object; and means for acquiring an illumination effect by causing a position to fluctuate within a predetermined partial area in terms of time, said illumination effect being substantially equivalent to incoherent illumination or partial coherent illumination, an illumination light-flux from said laser light-source being passing through said position on an illumination pupil plane, said pattern-defect inspection method, comprising a step of:

detecting a defect by making a comparison between a detected image and a reference image, said detected image being acquired with an imaging device by scanning patterns having the same configuration and arranged continuously with an equal spacing in row/column directions on said inspection-target object, said reference image being acquired with said imaging device by scanning patterns having the same configuration and being adjacent thereto in said row/column directions, wherein there is further provided means for measuring defect contrast by changing said partial area, said illumination light-flux from said laser light-source being caused to fluctuate within said partial area on said illumination pupil plane, said defect contrast being defined as a ratio of absolute value of a signal intensity difference with respect to signal intensity of the brightest portion on said reference image, said signal intensity difference being calculated between said detected image and said reference image at position of said microscopic defect to be detected; and determining said partial area so that said defect contrast will become substantially maximized, said illumination light-flux from said laser light-source being caused to fluctuate within said partial area on said illumination pupil plane;

said pattern-defect inspection method, further comprising a step of:

controlling said partial area in accordance with a result of said determination, said illumination light-flux from said laser light-source being caused to fluctuate within said partial area on said illumination pupil plane.

14. The microscopic-defect inspection method according to claim 13, wherein there is further provided means for measuring said signal intensity difference between said detected image and said reference image with a sign affixed thereto when measuring said defect contrast of said microscopic defect to be detected by changing said partial area, said illumination light-flux from said laser light-source being caused to fluctuate within said partial area on said illumination pupil plane, and determining said partial area so that said defect contrast will become substantially maximized in a combination of said signal intensity differences whose affixed signs become one and the same sign, said illumination light-flux from said laser light-source being caused to fluctuate within said partial area on said illumination pupil plane.

* * * * *